United States Patent [19]

Church

[11] 4,240,437
[45] Dec. 23, 1980

[54] ELECTRIC MASSAGE APPARATUS AND METHOD

[76] Inventor: Charles J. Church, P.O. Box 1214, Middleburg, Va. 22117

[21] Appl. No.: 929,146

[22] Filed: Jul. 31, 1978

Related U.S. Application Data

[63] Continuation-in-part of Ser. No. 819,912, Jul. 28, 1977, abandoned.

[51] Int. Cl.$^3$ ............................................. A61N 1/36
[52] U.S. Cl. ............................. 128/420 R; 128/421; 128/798
[58] Field of Search ............ 128/82.1, 419 F, 419 R, 128/420 R, 421, 422, 423 R, 783 N, 798, 799, 802, 803

[56] References Cited

U.S. PATENT DOCUMENTS

| | | | |
|---|---|---|---|
| 334,879 | 1/1886 | Mayer . | |
| 500,767 | 7/1893 | Hetherington-Carruthers . | |
| 533,791 | 2/1895 | Doehring . | |
| 548,777 | 10/1895 | Davis . | |
| 691,820 | 1/1902 | Spalding | 128/783 |
| 693,257 | 2/1902 | Gavigan | 128/802 |
| 1,853,815 | 4/1932 | Jackson . | |
| 1,975,518 | 10/1934 | Rose . | |
| 2,099,511 | 11/1937 | Caesar | 128/423 |
| 2,295,585 | 9/1942 | Lindquist . | |
| 3,025,858 | 3/1962 | Browner | 128/422 |
| 3,472,233 | 10/1969 | Sarbacher | 128/422 |
| 3,612,060 | 10/1971 | Colyer | 128/422 |
| 3,718,132 | 2/1973 | Holt et al. | 128/421 |
| 3,880,170 | 4/1975 | Popov . | |
| 3,893,462 | 7/1975 | Manning . | |
| 3,946,745 | 3/1976 | Hsiang-Lai et al. | 128/421 |
| 3,989,050 | 11/1976 | Buchalter | 128/803 |
| 4,155,366 | 5/1979 | DiMucci | 128/421 |

FOREIGN PATENT DOCUMENTS

| | | |
|---|---|---|
| 2500415 | 7/1976 | Fed. Rep. of Germany . |
| 2507783 | 9/1976 | Fed. Rep. of Germany . |
| 773082 | 4/1957 | United Kingdom . |
| 1479734 | 7/1977 | United Kingdom . |

*Primary Examiner*—William E. Kamm
*Attorney, Agent, or Firm*—Beveridge, De Grandi, Kline & Lunsford

[57] ABSTRACT

An apparatus for and a method of treatment of animals, including humans, with a pulsating electrical potential that is applied across electrodes placed on the animals. In a first embodiment the pulsating electrical potential has a first characteristic, including pulse repetition rate, pulse amplitude, and pulse polarity, for a first period of time and then a second characteristic, again including pulse repetition rate, pulse amplitude and pulse polarity, for a second period of time. In a second embodiment, the electrodes and their placement on the animal are controlled so that the electrical potential has a voltage-to-current ratio within an optimum range.

35 Claims, 13 Drawing Figures

ELECTRIC MASSAGE APPARATUS AND METHOD

CROSS-REFERENCE TO RELATED APPLICATIONS

This application is a continuation-in-part of U.S. patent application Ser. No. 819,912, filed July 28, 1977 now abandoned.

BACKGROUND OF THE INVENTION

The present invention pertains to an electrical massage apparatus and method. More particularly, the present invention pertains to an apparatus for and a method of treatment of animals, including humans, domesticated animals, and other animals to promote healing and to lessen the likelihood of injury, by applying a pulsating electrical potential across electrodes positioned on the animal, thereby reducing inflammation and providing a massaging effect.

Good circulation is an important factor in maintenance of good health. Good circulation not only aids maintaining physical soundness and prevention of injury but also aids swift repair of damaged tissue. Circulation includes the flow of both blood and lymph fluids. More than simply increased blood supply to a specific location is required for good circulation. Increased blood supply alone might result merely in unwanted scar tissue. The circulation of the blood is accomplished by the pumping action of the heart. However, the heart cannot cause circulation to be increased in one specific area without a corresponding increase in other areas, and localized increased circulation in an area of injury is desirable to aid healing. Such localized control of circulation can be accomplished by the action of the adjacent muscles and can be induced by electrical impulses. The equally important circulation of lymph fluids is not controlled by an organ such as the heart; however, it, too, can be brought about by the action of the muscles and by electrical impulses.

In animals other than humans, additional problems arise because the animals have relatively fewer blood and lymph vessels particularly in their legs, and because the animals cannot generally be inspired to exercise particular muscles or limbs to aid in circulation in a specific area. In some animals the problem is further aggravated by the normal routine of the animal. A horse, for example, might be confined within a stall for twenty or more hours of every day. During the majority of those twenty hours, the horse remains standing, adding to circulation problems.

Localized muscular exercise can be induced by applying slight electrical potential across selected locations on the animal. U.S. Pat. No. 2,623,525, for example, discloses apparatus for treating injuries in animals by use of faradic currents which cause rhythmatic muscular contractions. U.S. Pat. No. 3,893,462 discloses the use of alternating signals having a frequency in the range of 10 hertz to 10 kilohertz with electrodes placed on the surface of the animal remote from each other. While these and other prior art teach the use of electrical currents to induce healing in animals, generally each prior art device utilizes but a single type of electrical current and involves actual muscular contraction and relaxation of an individual muscle or group of muscles, rather than stimulating cells or tissues themselves.

SUMMARY OF THE INVENTION

It is thought that each body cell of an animal has a certain electrical energy level which can vary greatly according to the health and activity of the cell. The present invention seeks to maintain the balance of this electrical energy to the desired degree, particularly prior to and following periods of exertion. Further, the present invention seeks to correct the imbalance of electrical energy occurring during injury or disease. This also assists the increase in electrical energy that naturally occurs during the healing process.

The present invention is well suited for healing of injuries, and it likewise is well suited for maintenance of good health in animals not presently suffering from injuries. In the following specification and claims, then, the present invention is frequently referred to in conjunction with "treatment" of animals, the term "treatment" encompassing both healing of injuries and maintenance of sound health. Likewise, the term "animal" is used in its broad sense to encompass humans, large and small domesticated animals, and other animals. In general, the present invention involves the treatment of animals with a pulsating electrical potential having selected characteristics.

In one aspect of the present invention it has been found that improved treatment of animals is obtained by use of an electrical potential of a first characteristic for a first period of time followed by an electrical potential of a second characteristic for a second period of time. As a specific illustration of this aspect of the invention, it has been found that healing of bone cells is promoted, and the maintenance of sound health aided, when a first pulsating electrical potential in the range of from about zero volts to about eight volts and a pulse repetition rate in the range of from about 50 pulses per second to about 200 pulses per second, preferably in the order of about 180 pulses per second, is applied with a first polarity for a period of time in the range of from about fifteen minutes to about three hours across a first electrode positioned at one location on an animal and a second electrode positioned at a second location on the animal, with the first electrical potential being followed by a second pulsating electrical potential in the range of from about zero volts to about eight volts and a pulse repetition rate in the range of from about 50 pulses per second to about 200 pulses per second, preferably in the order of about 180 pulses per second, applied with a second polarity opposite the first polarity for a period of time in the range of from about thirty minutes to about three hours, preferably in the order of about one-and-a-half hours. Likewise, in accordance with this aspect of the present invention, it has been found that healing of soft tissue is promoted, and the maintenance of sound health aided, when a first pulsating electrical potential in the range of from about zero volts to about twenty volts and a pulse repetition rate in the range of from about twenty-five pulses per second to about 150 pulses per second, preferably in the order of about 100 pulses per second, is applied for a period of time in the range of from about fifteen minutes to about three hours across the two electrodes, followed by a second pulsating electrical potential in the range of from about zero volts to about twenty volts and a pulse repetition rate of up to about 150 pulses per second, preferably in the order of about twenty-five pulses per second applied for a period of time of up to about three or four hours. By "soft tissue" is meant tendons and cartilage etc., but not muscle. In general, in this aspect of the present invention, the electrical potential assumes a first characteristic, having a first pulse repetition rate and a first pulse amplitude, applied with a first polarity across the two electrodes for a first period of time, and then a second characteristic, having a second pulse repetition rate and a second pulse amplitude, applied with a second polarity across the electrodes for a second period of time, any one or more of the pulse repetition rate, pulse amplitude, and pulse polarity not necessarily being different between the first characteristic of the electrical potential and the second characteristic.

In a second aspect of the present invention, it has additionally been found that improved healing and enhanced health maintenance are obtained by use of an electrical potential coupled across an appropriate portion of the animal with optimum coupling characteristics, such that the ratio of the applied voltage to the applied current, as measured at the output of the electrical potential source, falls within an optimum range. By way of example, for horses it has been found that optimum healing and health maintenance are achieved when the voltage-to-current ratio is maintained less than about 2500 volts per ampere.

BRIEF DESCRIPTION OF THE DRAWINGS

These and other aspects and advantages of the present invention are more apparent in the following detailed description and claims, particularly when considered in conjunction with the accompanying drawings in which like parts bear like reference numerals. In the drawings:

FIG. 1 depicts apparatus in accordance with the present invention attached to an animal, illustratively depicted as a horse 10. The apparatus includes first and second flexible sock members 12 which are wrapped and fastened about the forelegs 14 of horse 10. The apparatus of the present invention further includes a flexible member 16 which is fastened on the trunk of horse 10 by means of a strap 18. A housing 20 is fastened to flexible member 16 to be positioned on the withers of horse 10. Housing 20 encloses the electrical circuitry utilized in the apparatus of the present invention, and that circuitry is electrically connected by leads 22 to electrodes within sock members 12 and is electrically connected to an electrode within flexible member 16.

Each sock member 12 is formed of a suitable flexible material, for example a sponge rubber, enclosed within a casing of, for example, nylon. As illustrated in FIG. 2, each sock member 12 includes a flexible body portion 24 and a suitable fastening means such as straps 26 for fastening the sock member about a limb of an animal. Alternatively, other fastening means, for example Velcro strips, or a flexible bandage, could be used.

A first electrode 28 is provided on one surface of flexible body portion 24 to contact the animal when sock member 12 is positioned on the animal. Electrode 28 might be formed of suitable flexible material such as an electrically conductive rubber or other suitable material. Electrode 28 is electrically connected to a lead 22. FIG. 2 depicts a single rectangular electrode 28, but plural electrodes and other shapes could be utilized, for example two or more electrodes which might be circular, oval or any other desired shape.

FIG. 3 depicts flexible member 16 which is provided with two electrodes 30 on one surface thereof. While FIG. 2 illustrates two rectangular electrodes 30, a single electrode member, or a larger number of electrode members, and other shapes, might be utilized, if desired. Again, electrodes 30 are formed of a suitable flexible material such as an electrically conductive rubber and are electrically connected to the electrical circuitry within housing 20. The one or more electrodes 28 within sock member 12 might have a total surface area in the range of from about four square inches to about 40 square inches, and the one or more electrodes 30 within flexible member 16 might have a total surface area in the same range.

Figure 1:
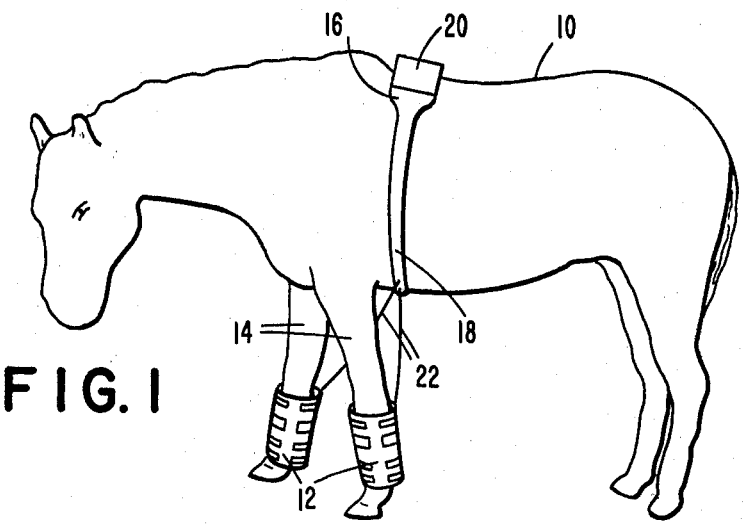
FIG. 1 is a perspective view of an animal having fastened thereon apparatus in accordance with the present invention.

In the treatment of an animal, such as horse 10, in accordance with the present invention, one or more sock members 12 are positioned on the animal, for example wrapped about one or more of the limbs 14 of the animal, and flexible member 16, with housing member 20 attached thereto, is likewise positioned on the animal, for example, on the trunk of the animal with electrodes 30 contacting the withers during utilization of the present invention on a horse. It is not required that the electrodes 28 and 30 contact the leg and the withers of the animal; one electrode should be at a first location adjacent the area to be treated, while the second electrode is at a second location remote from the first location. The locations on the animal which are to contact electrodes 28 and 30 are first wetted and coated with a contact jelly or electrode jelly. Once the one or more sock members 12 and the flexible member 16 are fastened in position, the circuitry within housing 20 is activated to cause a pulsating electrical potential between electrodes 28 and 30.

In accordance with a first aspect of the present invention, the pulsating electrical potential applied across electrodes 28 and 30 has a first characteristic for a first preset time and a second characteristic for a second preset time, following which the electrical circuitry is deactivated.

In the treatment of bones in accordance with this aspect of the invention, the electrical potential applied across electrodes 28 and 30 has a first characteristic, preferably with a pulse repetition rate in the range of from about 50 pulses per second to about 200 pulses per second, more preferably in the order of about 180 pulses per second, and a pulse amplitude in the range of from about zero volts to about eight volts for a period of time in the range of from about fifteen minutes to about three hours during which the electrode that is applied adjacent the area of treatment is electrically positive with respect to the other electrode, followed by a second characteristic, preferably with a pulse repetition rate in the range of from about 50 pulses per second to about 200 pulses per second, more preferably in the order of about 180 pulses per second, and a pulse amplitude in the range of from about zero volts to about eight volts for a period of time in the range of from about thirty minutes to about three hours, preferably in the order of about one-and-a-half hours during which the electrode that is applied adjacent the area of treatment is electrically negative with respect to the other electrode. If the foreleg of the horse is being treated in FIG. 1, then, of course, electrode 28 within sock member 12 is "the electrode that is applied adjacent the area of treatment."

In the treatment of soft tissue in accordance with this aspect of the present invention, the electrical potential applied across electrodes 28 and 30 has a first characteristic, preferably with a pulse repetition rate in the range of from about twenty-five pulses per second to about 150 pulses per second, more preferably in the order of about 100 pulses per second, and a pulse amplitude in the range of from about zero volts to about twenty volts, for a period of time in the range of from about fifteen minutes to about three hours, followed by a second characteristic, with a pulse repetition rate of up to about 150 pulses per second, preferably in the order of about twenty-five pulses per second, and a pulse amplitude in the range of from about zero volts to about twenty volts, for a period of time in the order of about three hours. For maintenance of good condition, two or more legs might be treated simultaneously by two or more sock members 12, as depicted in FIG. 1, with the electrodes 28 within the several sock members 12 maintained at substantially the same electrical potential. To promote healing, a single sock member 12 might be utilized on an injured limb of an animal.

Figure 4:
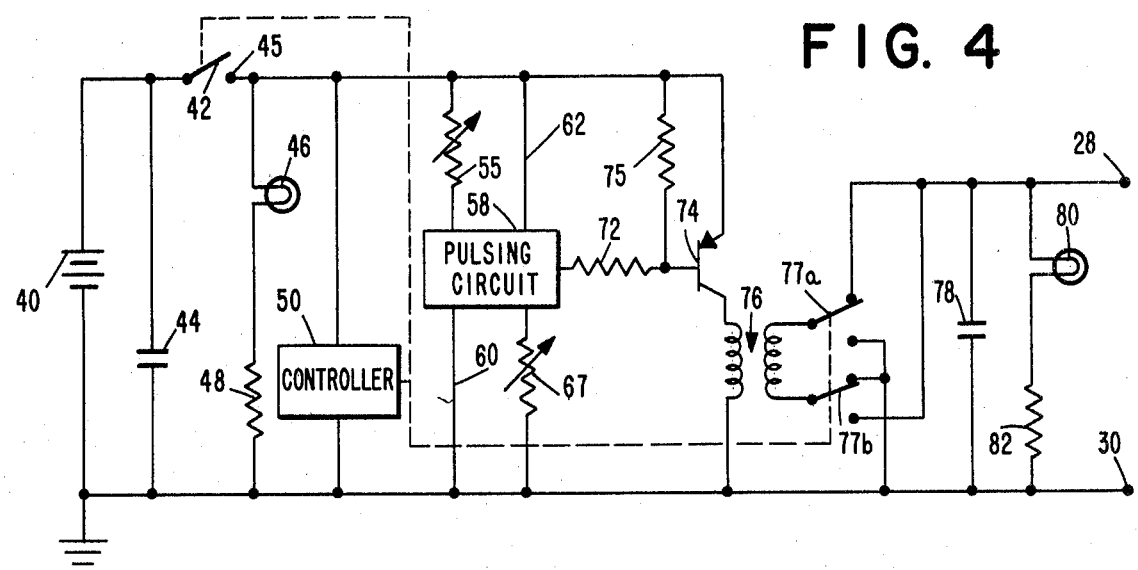
FIG. 4 is a schematic diagram illustrative of one embodiment of circuitry suitable for incorporation into apparatus for treatment of bone in accordance with a first aspect of the present invention.

FIG. 4 illustratively depicts circuitry suitable for use in an apparatus in accordance with the present invention for treatment of bone. A source 40 of D.C. potential has its positive terminal connected to one contact of a switch 42 and its negative terminal tied to ground. Preferably, a capacitor 44 is connected across electrical potential source 40. Source 40 might be a battery, and, preferably, it provides a voltage in the order of about fifteen volts. The second terminal 45 of switch 42 is connected to one contact of an indicator 46 such as a light. The second contact of indicator 46 is coupled through a resistor 48 to ground. Indicator 46 is therefore energized whenever switch 42 is closed. Controller 50 is connected between contact 45 and ground. Once switch 42 is closed to energize controller 50, the controller causes switch 42 to open after a predetermined time, as more fully set forth hereinafter. Variable resistor 55 has its first terminal connected to switch contact 45 and its other terminal connected to one terminal of pulsing circuit 58. Lead 60 connects a second terminal of pulsing circuit 58 to ground. Lead 62 connects switch contact 45 to another terminal of pulsing circuit 58 to provide electrical potential thereto. Variable resistor 67 couples a fourth terminal of pulsing circuit 58 to ground.

The output terminal of pulsing circuit 58 is coupled by resistor 72 to the base of NPN transistor 74. Transistor 74 also has its base coupled to switch contact 45 by resistor 75, its emitter tied to switch contact 45, and its collector coupled to ground by the primary winding of transformer 76. The secondary winding of transformer 76 is coupled between the two moving contacts 77a and 77b of a double-pole-double-throw switch which is controlled by controller 50. Moving contact 77a has its first fixed contact connected to electrode 28 and its second fixed contact connected to electrode 30. Likewise, moving contact 77b has its first fixed contact connected to electrode 30 and its second fixed contact connected to electrode 28. Preferably, a capacitor 78 is connected between electrodes 28 and 30, and an indicator 80, such as a light bulb, has one of its contacts connected to electrode 28 and its other contact coupled by resistor 82 to electrode 30.

Pulsing circuit 58 is a conventional pulsing circuit such as a unijunction transistor pulsing circuit or such as a commercially available circuit, for example a suitably adapted NE555 circuit available from Signetics Corporation of Sunnyvale, Calif. Variable resistor 55 permits control of the output pulse repetition rate, while variable resistor 67 permits control of the output pulse amplitude.

Figure 5:
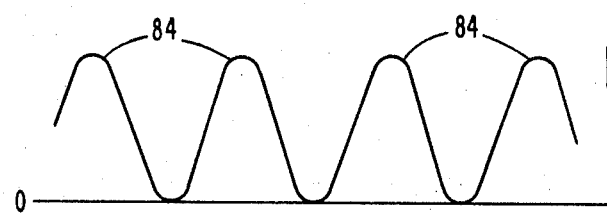
FIG. 5 is a diagram depicting an output voltage waveform realizable from the apparatus of FIG. 4.

Each output pulse from pulsing circuit 58 is applied by resistor 72 to the base of transistor 74, and so each output pulse from circuit 58 results in a pulse across the primary winding of transformer 76. A corresponding electrical potential pulse is induced in the secondary winding of transformer 76 and appears across electrodes 28 and 30, as depicted by pulses 84 in FIG. 5. With moving contacts 77a and 77b closed against their respective first fixed contacts, as depicted in FIG. 4, these pulses are applied across electrodes 28 and 30, with electrode 28 positive with respect to electrode 30. The pulses are not sharp but are more nearly sinesoidal. The pulses are, however, only of one polarity, as seen in FIG. 5. With contacts 77a and 77b closed against their respective second fixed contacts, the pulses 84 are applied across electrodes 28 and 30 with electrode 30 positive with respect to electrode 28.

Controller 54 includes suitable timing circuitry to cause switch contacts 77a and 77b to change position after a first preset time and to open switch 42 after a second preset time. Accordingly, once switch 42 is manually closed with moving contacts 77a and 77b closed to their respective first fixed contacts, pulses 84, of a first pulse repetition rate, determined by the setting of variable resistor 55, and of a first amplitude, determined by the setting of variable resistor 67, are applied across electrodes 28 and 30, with electrode 28 positive with respect to electrode 30, for the first preset time, and then moving contacts 77a and 77b are closed to their respective second fixed contacts so that pulses 84, of the first pulse repetition rate and first pulse amplitude, are applied across electrodes 28 and 30, with electrode 30 positive with respect to electrode 28, for the second preset time, following which switch 42 is opened to deactivate the circuit. Indicator 80 is energized by each pulse.

Figure 6:
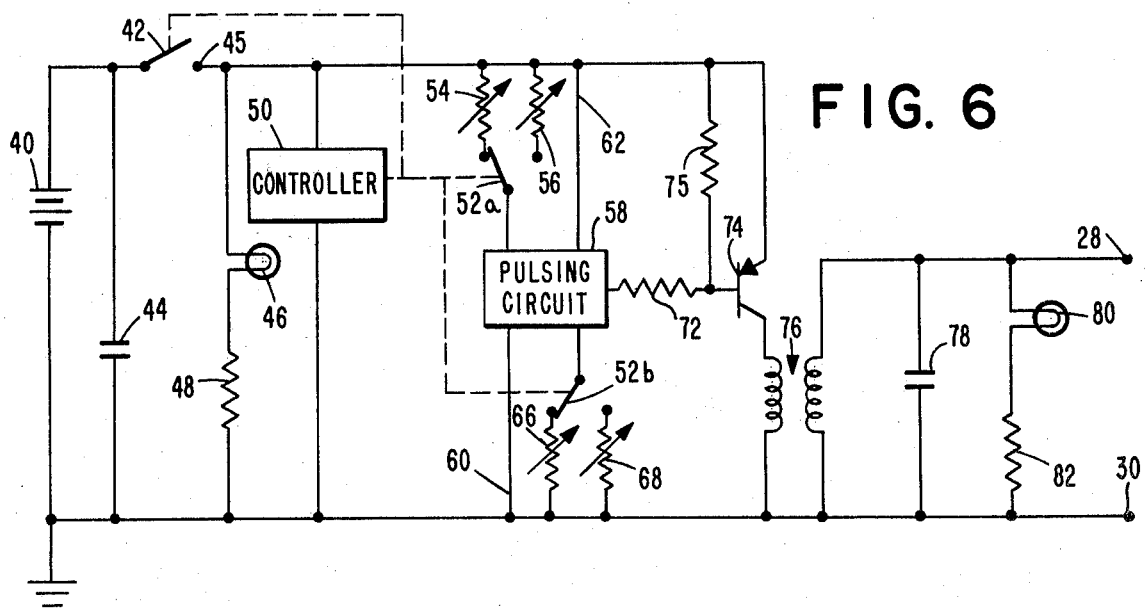
FIG. 6 is a schematic diagram illustrative of another embodiment of circuitry suitable for incorporation into apparatus for treatment of soft tissue in accordance with this aspect of the present invention.

FIG. 6 illustratively depicts similar circuitry suitable for use in an apparatus in accordance with the present invention for treatment of soft tissue. Again, source 40 of D.C. potential has its positive terminal connected to one contact of a switch 42 and its negative terminal tied to ground, and capacitor 44 is preferably connected across electrical potential source 40. Indicator 46 and resistor 48 are connected in series between the second terminal 45 of switch 42 and ground so that indicator 46 is energized whenever switch 42 is closed. Controller 50 is connected between contact 45 and ground to be energized when switch 42 is closed, and so once switch 42 is closed to energize controller 50, the controller causes switch 42 to open after a predetermined time.

Controller 50 controls the first moving contact 52a and the second moving contact 52b of a double-pole-double-throw switch. Contact 52a has its first fixed contact coupled by variable resistor 54 to switch contact 45 and its second fixed contact coupled by variable resistor 56 to switch contact 45. Moving contact 52a is connected to one terminal of pulsing circuit 58, which has a second terminal connected to ground by lead 60. Lead 62 connects switch contact 45 to another terminal of pulsing circuit 58 to provide electrical potential thereto. Contact 52b has its first fixed contact coupled to ground by variable resistor 66 and its second fixed contact coupled to ground by variable resistor 68. Moving contact 52b is tied to a further terminal of pulsing circuit 58.

The output terminal of pulsing circuit 58 is coupled by resistor 72 to the base of NPN transistor 74. Transistor 74 also has its base coupled to switch contact 45 by resistor 76, its emitter tied to switch contact 45, and its collector coupled to ground by the primary winding of transformer 76. The secondary winding of transformer 76 is coupled between electrode 28 and electrode 30. Likewise, capacitor 78 is coupled between electrodes 28 and 30, and indicator 80 and resistor 82 are connected in series between electrode 28 and electrode 30.

Variable resistors 54 and 56 and switch contact 52a permit control of the output pulse repetition rate of pulsing circuit 58, while variable resistors 66 and 68 and switch contact 52b permit control of the output pulse amplitude. Switch contacts 52a and 52b permit utilization of either a first pulse repetition rate, determined by the setting of variable resistor 54, and a first pulse amplitude, determined by the setting of variable resistor 66, or a second pulse repetition rate, determined by the setting of variable resistor 56, and a second pulse amplitude, determined by the setting of variable resistor 68. The variable resistors can, of course, be set to cause either the same or different pulse repetition rates and either the same or different pulse amplitudes, as desired for the two positions of the switch contacts 52a and 52b.

Figure 7:
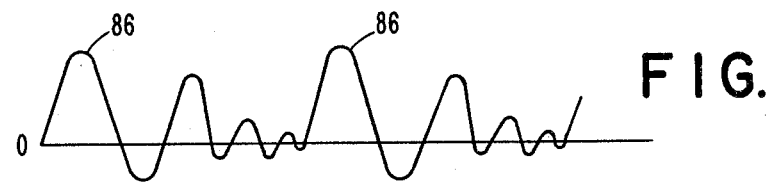
FIG. 7 is a diagram depicting an output voltage waveform realizable from the apparatus of FIG. 6.

Again, each pulse from pulsing circuit 58 controls transistor 74 so that each output pulse from circuit 58 results in a pulse across the primary winding of transformer 76, inducing a corresponding electrical potential pulse in the secondary winding of the transformer which appears across electrodes 28 and 30, as depicted by pulses 86 in FIG. 7. By way of example, electrode 28 can be positive with respect to electrode 30 during each pulse 86, but, again, the pulses are not sharp, and some ringing occurs, with electrode 28 briefly swinging negative with respect to electrode 30, as depicted in FIG. 7.

Controller 54 includes suitable timing circuitry to cause switch contacts 52a and 52b to change position after a first preset time and to open switch 42 after a second preset time. Accordingly, once switch 42 is manually closed with moving contacts 52a and 52b closed to their respective first fixed contacts, pulses 86 of a first pulse repetition rate, determined by the setting of variable resistor 54, and a first pulse amplitude determined by the setting of variable resistor 66, are applied across electrodes 28 and 30 for a first preset time. Then controller 50 closes moving contacts 52a and 52b to their respective second fixed contacts, and pulses 86 of a second pulse repetition rate and a second pulse amplitude are applied across electrodes 28 and 30 for the second preset time, following which switch 42 is opened to deactivate the circuit.

While the switch contacts 52a, 52b, 77a and 77b have been depicted as mechanical switches, preferably they are electronic devices so that no mechanical switching is necessary when the pulse characteristics are switched. Likewise, while a single switch 42 has been depicted, which is closed manually and opened by controller 50, a series-connected set could be utilized, including a manually-actuable switch and an electronically-actuable switch operated under control of controller 50. Although the bone treatment circuitry and the soft tissue treatment circuitry have been shown separately in FIGS. 4 and 6, they have many common components, and by optimising the design, they might be combined into a single, dual-purpose apparatus. While FIG. 1 shows the animal 10 having two sock members 12 on its two forelegs 14, the sock members might be utilized on the hind legs or on a foreleg and a hind leg, or three or four socks might be utilized simultaneously on the animal. Additionally, rather than being positioned on legs of the animal one or more flexible sock members 12 could be positioned elsewhere on the animal, for example in a flattened condition.

Figure 2:
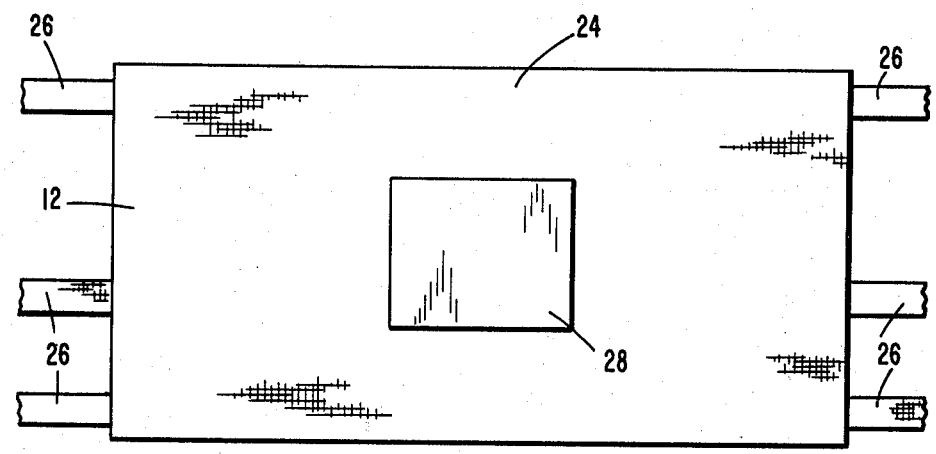
FIG. 2 is a plan view of a first flexible member suitable to form a part of the apparatus of the present invention.
Figure 3:
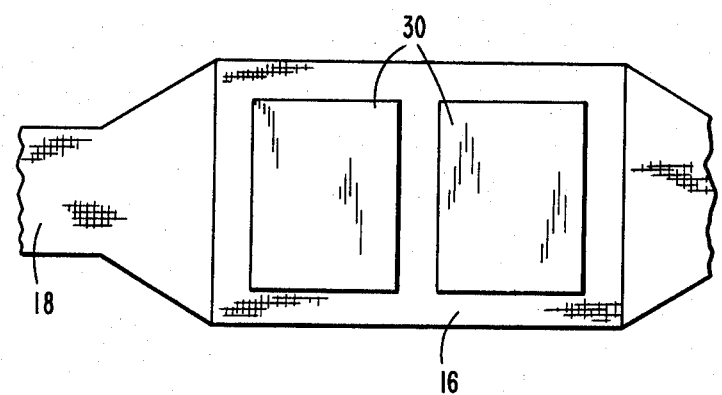
FIG. 3 is a plan view of a second flexible member suitable to form a part of the apparatus of the present invention.
Figure 8:
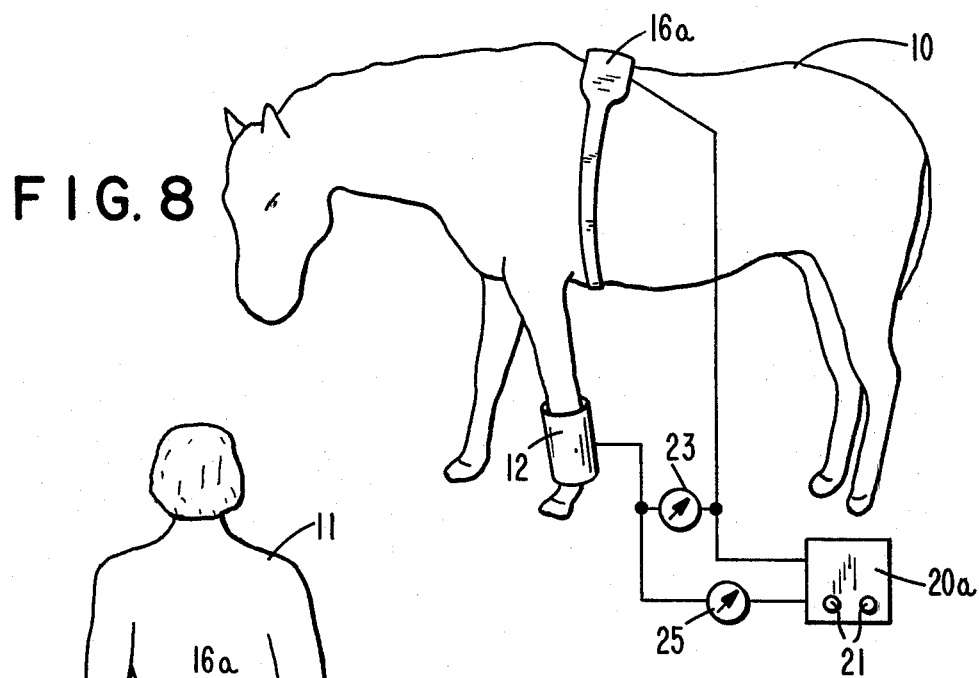
FIG. 8 is a diagrammatic representation of apparatus in accordance with the present invention utilized in treatment of a horse and illustrating the measuring of circuit parameters.
Figure 9:
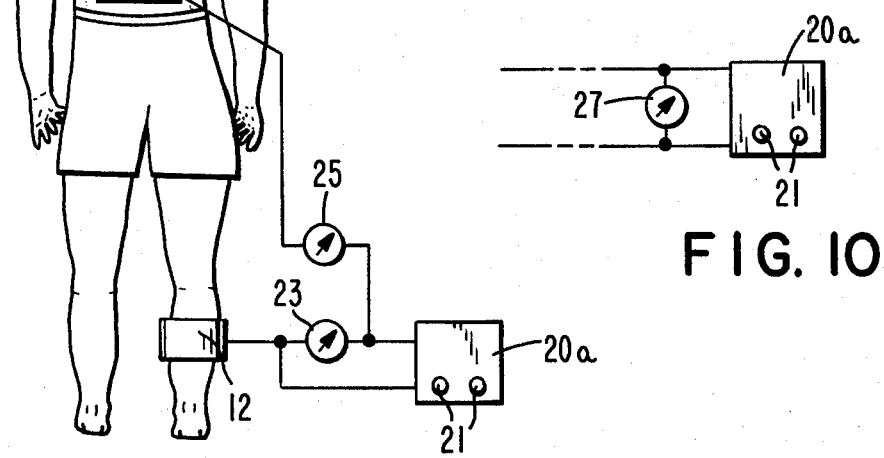
FIG. 9 is a similar diagrammatic representation of apparatus in accordance with the present invention utilized in treatment of a human and likewise illustrating the measuring of circuit parameters.

It has been found that optimum treatment of animals in accordance with the present invention is achieved when the ratio of the applied voltage to the applied current is within an optimum range. This voltage-to-current ratio can be determined by measuring the two parameters separately or by measuring the load resistance seen by the electronic circuitry in housing 20, across terminals 28 and 30. FIG. 8 schematically depicts treatment of a horse 10 in accordance with the present invention with apparatus including a flexible sock member 12, having an electrode such as electrode 28 of FIG. 2 therein, and a flexible member 16a, having an electrode such as electrode 30 therein. The electronic circuitry is contained within housing 20a which is coupled to electrodes 28 and 30. Housing 20a includes controls 21 for the electronic circuitry. Voltmeter 23 is coupled across the output of the electronic circuitry to register the applied voltage across electrodes 28 and 30, and ammeter 25 is connected in the lead from the electronic circuitry to one of the electrodes 28 or 30 to measure the current applied to horse 10 by the electrodes. In like manner, FIG. 9 schematically depicts a human 11 having flexible sock member 12 on one leg and flexible member 16a on his trunk. Electrodes 28 and 30 of sock member 12 and flexible member 16a are connected to the electronic circuitry within housing 20a, just as in FIG. 8. Likewise, voltmeter 23 is coupled across electrodes 28 and 30 to register the applied voltage across the electrodes, and ammeter 25 is connected in the lead from the electronic circuitry to one of the electrodes 28 or 30 to measure the current applied to the person.

Figure 10:
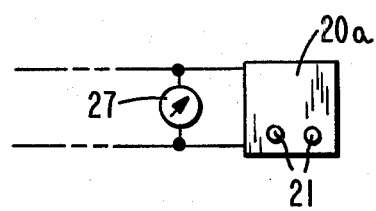
FIG. 10 depicts a slightly modified form of the apparatus of FIGS. 8 and 9.

FIG. 10 illustrates an alternative arrangement in which voltmeter 23 and ammeter 25 are replaced by ohmmeter 27 coupled across electrodes 28 and 30 to measure the load resistance seen by the electronic circuitry within housing 20a.

It has been found that optimum treatment is achieved if the ratio of the output voltage, read on voltmeter 23, to the current, read on ammeter 25, or the load resistance as indicated by ohmmeter 27, falls within an optimum range. More particularly, in the treatment of horses, it has been found that optimum treatment is achieved if this ratio of voltage-to-current is maintained less than about 2,500 volts per ampere, preferably less than about 2,000 volts per ampere. Likewise, in the treatment of humans, it has been found that optimum treatment is achieved if the ratio of voltage-to-current is maintained less than about 35,000 volts per ampere. An optimum range or limit is believed to exist for all animals, and, by way of example, tests have indicated that for small domesticated animals, such as cats and dogs, the optimum ratio of voltage-to-current is less than about 10,000 volts per ampere.

Various parameters can be controlled somewhat to obtain fine adjustment of the voltage-to-current ratio. Thus, for example, the extent to which the contact area is first wetted with an electrode jelly, and the tightness with which the flexible members 12 and 16 are in contact with the skin surface of the animal affect the voltage-to-current ratio. Accordingly, fine adjustment of the voltage-to-current ratio might be obtained by varying parameters such as these.

Figure 11A:
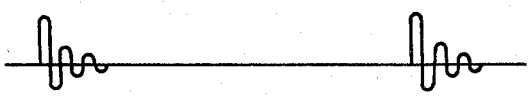
FIGS. 11A, 11B, and 11C are diagrams depicting voltage waveforms usable in treatment of animals in accordance with the present invention.
Figure 11B:
Figure 11C:
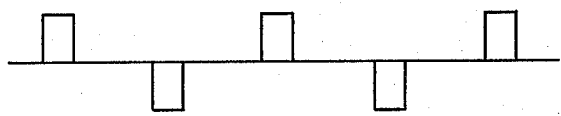

Utilizing the optimum voltage-to-current ratio falling within the limits set forth above, it has been found that beneficial treatment of animals is achieved with various voltage waveforms. FIGS. 11A, 11B, and 11C depict waveforms which have been utilized successfully. Thus, FIG. 11A depicts an overdamped sinusoid. Such a waveform might be utilized with a ringing time in the order of about one-half millisecond to about two milliseconds, a peak value of about 6 volts, and a pulse period in the order of about 10 milliseconds. FIG. 11B depicts a pulse waveform, with each pulse having a duration in the order of about one-half millisecond to about two milliseconds, a pulse period of about five milliseconds, and a pulse amplitude of about 9 volts. FIG. 11C depicts an alternating pulse waveform, with each pulse having a duration of about one-half millisecond to about one millisecond, with a pulse period, between consecutive pulses of the same polarity, in the range of from about 5 milliseconds to about 50 milliseconds, and with a peak-to-peak voltage of about 9 volts.

It has been found that optimum treatment of horses is achieved if the voltage pulse amplitude is in the range of from about two volts to about fifteen volts. Likewise, in treatment of humans, the optimum voltage is believed to be in the range of from about two volts to about 40 volts. It has likewise been found that improved treatment is achieved if these pulses are applied so that the electrode 28 or 30 adjacent the area being treated is pulsed electrically negative with respect to the other electrode. Thus, in the arrangement of FIG. 8, the pulses, for example of the type depicted in FIG. 11B, are applied so that, in treatment of a leg, the electrode within flexible sock member 12 becomes electrically negative with respect to the electrode in flexible member 16a. It is believed that such negative pulses step up cell activity and thus promote healing, although this theory has not been entirely verified. If, for example, the trunk or back of the horse is to be treated, the electrode on the trunk is pulsed negative with respect to the other electrode. The polarity of the pulses can be controlled by controlling the flexible member 12 or 16 in which the negatively pulsed electrode is placed or by controlling the location on the animal at which each flexible member is positioned or by switching within the circuitry in housing 20.

Treatment with waveforms of FIG. 11A, 11B, or 11C has been found to be effective without reversal of polarity. Thus, treatment might consist of application of such waveforms for a period in the order of from about thirty minutes to about three hours.

More effective treatment has been found to occur with a short period of positive potential pulses applied to the area of treatment followed by a longer period of negative potential pulses. It has also been found that an alternating current having a slight bias, such as depicted in FIG. 7, is effective, particularly for maintenance of good health, with the negative-going electrode adjacent the area undergoing treatment. In order to achieve the optimum effectiveness presently found from treatment in accordance with the present invention, the area undergoing treatment should have applied to it every day for three to four days first positive-potential pulses for fifteen to thirty minutes, then negative potential pulses for one to three hours. This treatment would then be followed by application of negative potential pulses every day for up to about seventeen days, after which maintenance is aided by application of alternating pulses, such as in FIG. 7, with the negative bias applied to the area undergoing treatment, or such as in FIG. 11C, for one to three hours every day for as long as desired.

Although the present invention has been described with reference to the preferred embodiments, numerous modifications and rearrangements might be made, and still the result would come within the scope of the invention.

What is claimed is:

1. Apparatus for treatment of animals comprising:
   first electrode means;
   a first flexible member adapted to be fastened on an animal to hold said first electrode means in contact therewith;
   second electrode means;
   a second flexible member adapted to be fastened on the animal to hold said second electrode means in contact therewith;
   circiuit means connected to said first electrode means and to said second electrode means and capable of assuming an off condition, in which no electrical potential is applied across said first and second electrode means, a first on condition, in which a pulsating electrical potential having a first pulse characteristic, including pulse repetition rate, pulse amplitude, and pulse polarity, is applied across said first and second electrode means, and a second on condition, in which a pulsating electrical potential having a second pulse characteristic, including pulse repetition rate, pulse amplitude, and pulse polarity, is applied across said first and second electrode means; and
   control means connected to said circuit means and activatable to cause said circuit means to assume its first on condition for a first preset time, to then assume its second on condition for a second preset time, and to then assume its off condition.

2. Apparatus as claimed in claim 1 further comprising:

third electrode means; and a third flexible member adapted to be fastened on the animal to hold said third electrode means in contact therewith, said third electrode means connected to said circuit means to be at substantially the same electrical potential as said first electrode means.

3. Apparatus as claimed in claim 1 in which said first flexible member comprises a sock member adapted to be wrapped about a limb of the animal.

4. Apparatus as claimed in claim 1 in which said first and second flexible members are formed of sponge rubber.

5. Apparatus as claimed in claim 1 in which each electrode means is formed of an electrically conductive rubber.

6. Apparatus as claimed in claim 1 further comprising a housing member attached to one of said flexible members, said circuit means and said control means being within said housing member.

7. Apparatus as claimed in claim 1 in which said circuit means includes a means for varying the pulse repetition rate.

8. Apparatus as claimed in claim 7 in which said circuit means further includes means for varying the pulse amplitude.

9. Apparatus as claimed in claim 1 in which said circuit means includes means for varying the pulse amplitude.

10. Apparatus as claimed in claim 1 in which said control means includes means for changing the pulse repetition rate between said first pulse characteristic and said second pulse characteristic.

11. Apparatus as claimed in claim 10 in which said control means further includes means for changing the pulse amplitude between said first pulse characteristic and said second pulse characteristic.

12. Apparatus as claimed in claim 1 in which said control means includes means for changing the pulse amplitude between said first pulse characteristic and said second pulse characteristic.

13. Apparatus as claimed in claim 1 in which said control means includes means for changing the pulse polarity between said first pulse characteristic and said second pulse characteristic.

14. Apparatus as claimed in claim 1 in which said control means includes timer means activated when said circuit means assumes its first on condition to automatically cause said circuit means to assume its second on condition after the first preset time and then to automatically cause said circuit means to assume its off condition after the second preset time.

15. A method of treatment of animals to promote healing of injuries and maintenance of sound health comprising the steps of:

(a) placing a first electrode on a first location on the animal;

(b) placing a second electrode on a second location on the animal;

(c) applying across the first and second electrodes for a first period of time a pulsating electrical potential having a first pulse characteristic, including pulse repetition rate, pulse amplitude, and pulse polarity; and (d) applying across the first and second electrodes for a second period of time a pulsating electrical potential having a second pulse characteristic, including pulse repetition rate, pulse amplitude, and pulse polarity, said second pulse characteristic being different from said first pulse characteristic in at least one of the pulse repetition rate, the pulse amplitude, and the pulse polarity.

16. A method as claimed in claim 15 in which step (a) comprises placing the first electrode on a limb of the animal and step (b) comprising placing the second electrode on the trunk of the animal.

17. A method as claimed in claim 16 further comprising the steps of:

(e) placing a third electrode on a second limb of the animal; and (f) maintaining the third electrode at substantially the same electrical potential as the first electrode.

18. A method as claimed in claim 15 in which step (a) comprises placing the first electrode on a leg of the animal and step (b) comprises placing the second electrode on the withers of the animal.

19. A method as claimed in claim 18 in which each of steps (a) and (b) comprises placing the electrode on a horse.

20. A method as claimed in claim 15 in which step (a) comprises placing the first electrode on a foreleg of the animal and step (b) comprises placing the second electrode on the withers of the animal.

21. A method as claimed in claim 20 in which each of steps (a) and (b) comprises placing the electrode on a horse.

22. A method as claimed in claim 15 in which steps (a) and (b) comprises wetting said first and second locations on the animal, coating said first and second locations with electrode jelly, and fastening the electrodes in contact with said jelly coated locations to place the electrodes on the animal.

23. A method as claimed in claim 15 in which the first pulse characteristic has a pulse repetition rate in the range of from about 50 pulses per second to about 200 pulses per second.

24. A method as claimed in claim 23 in which the first pulse characteristic has a pulse repetition rate in the order of about 180 pulses per second.

25. A method as claimed in claim 24 in which the second pulse characteristic has a pulse repetition rate in the order of about 180 pulses per second and a pulse polarity opposite the pulse polarity of the first pulse characteristic.

26. A method as claimed in claim 23 in which the second pulse characteristic has a pulse repetition rate in the range of from about 50 pulses per second to about 200 pulses per second.

27. A method as claimed in claim 23 in which the first pulse characteristic has a pulse amplitude of less than about eight volts.

28. A method as claimed in claim 27 in which the second pulse characteristic has a pulse repetition rate in the range of from about 50 pulses per second to about 200 pulses per second, a pulse amplitude of less than about eight volts, and a pulse polarity opposite the pulse polarity of the first pulse characteristic.

29. A method as claimed in claim 15 in which the second pulse characteristic has a pulse polarity opposite the pulse polarity of the first pulse characteristic.

30. A method as claimed in claim 15 in which the first pulse characteristic has a pulse reptition rate in the range of from about twenty-five pulses per second to about 150 pulses per second.

31. A method as claimed in claim 30 in which the first pulse characteristic has a pulse repetition rate in the order of about 100 pulses per second.

32. A method as claimed in claim 31 in which the second pulse characteristic has a pulse repetition rate in the order of about 25 pulses per second.

33. A method as claimed in claim 30 in which the first pulse characteristic has a pulse amplitude of less than about twenty volts.

34. A method as claimed in claim 30 in which the second pulse characteristic has a pulse repetition rate in the range of less than about 150 pulses per second.

35. A method as claimed in claim 34 in which the second pulse characteristic has a pulse amplitude in the order of about twenty volts.

* * * * *